United States Patent [19]
Amano et al.

[11] Patent Number: 5,571,108
[45] Date of Patent: Nov. 5, 1996

[54] BINOCULAR STEREO MICROSCOPE

[75] Inventors: Masanori Amano; Akira Yabusaki, both of Gamagori, Japan

[73] Assignee: Nidek Co., Ltd., Gamagori, Japan

[21] Appl. No.: 246,568

[22] Filed: May 20, 1994

Related U.S. Application Data

[63] Continuation of Ser. No. 23,684, Feb. 26, 1993, abandoned.

[30] Foreign Application Priority Data

Feb. 29, 1992 [JP] Japan ................ 4-079044

[51] Int. Cl.⁶ .............. A61N 5/02; G06K 9/00
[52] U.S. Cl. .............................. 606/10; 606/4
[58] Field of Search ............... 606/2, 3, 4, 5, 606/6, 10, 11, 12, 17

[56] References Cited

U.S. PATENT DOCUMENTS

| | | | |
|---|---|---|---|
| 3,796,220 | 3/1974 | Bredemeir | 606/18 |
| 3,828,788 | 8/1974 | Krasnov et al. | 606/4 |
| 4,443,075 | 4/1984 | Crane | 606/18 |
| 4,477,159 | 10/1984 | Mizuno et al. | 606/4 |
| 4,520,816 | 6/1985 | Schachar et al. | 606/4 |
| 4,554,917 | 11/1985 | Tagnon | 606/4 |
| 4,638,801 | 1/1987 | Daly et al. | 606/4 |
| 4,848,340 | 7/1989 | Bille et al. | 606/4 |
| 4,870,964 | 10/1989 | Bailey, Jr. et al. | 606/4 |
| 4,880,001 | 11/1989 | Weinberg | 606/11 |
| 4,887,592 | 12/1989 | Loertscher | 606/5 |
| 4,931,053 | 6/1990 | L'Esperance, Jr. | 606/4 |
| 5,013,319 | 5/1991 | Davis | 128/898 |
| 5,026,368 | 6/1991 | Adair | 606/15 |
| 5,029,220 | 7/1991 | Juday | 606/6 |
| 5,098,426 | 3/1992 | Sklar et al. | 606/4 |

FOREIGN PATENT DOCUMENTS

| | | |
|---|---|---|
| 64-58255(A) | 3/1989 | Japan . |
| 3-218744(A) | 9/1991 | Japan . |

Primary Examiner—Angela D. Sykes
Assistant Examiner—Sonya Harris-Ogugua
Attorney, Agent, or Firm—Finnegan, Henderson, Farabow, Garrett and Dunner, L.L.P.

[57] ABSTRACT

Binocular stereo microscope including an observation optical system to observe the patient's eye through binocular vision, comprising laser transmitting optical system for transmitting the therapeutic laser beam coaxially with the optical axis of an objective lens in the binocular stereo microscope to the patient's eye, alignment light beam projection optical system for projecting the alignment light beam onto the patient's eye to form an alignment index on the eye. CCD detects the index image projected on the patient's eye by the alignment light beam projection optical system, CPU judges alignment situation based on the image detected by the CCD, moving unit for moving the patient's eye relatively to the binocular stereo microscope is moved based on a judgement of the CPU.

15 Claims, 4 Drawing Sheets

BINOCULAR STEREO MICROSCOPE

This application is a continuation, of application Ser. No. 08/023,684, filed Feb. 26, 1993, now abandoned.

BACKGROUND OF THE INVENTION

1. Field of the Invention

The present invention relates to a binocular stereo microscope to observe an eye to be operated on, and more particularly to an alignment structure of a binocular stereo microscope provided in an operation apparatus for operating on a cornea and the like to change the curvature of the cornea.

2. Description of Related Art

Conventionally, there are many kinds of binocular stereo microscopes used in the conventional operation apparatus for operating on the cornea. Regarding the alignment of such binocular stereo microscope to arrange the eye to be operated on and the laser beam transmitting optical system for transmitting the therapeutic laser beam into the eye to be operated on relatively in a proper position, the following methods have been proposed.

For example, one method is adjusting a reticule inserted into one eyepiece part of the observation optical system in the binocular stereo microscope to the illumination light image reflected by the cornea or an image of the anterior eye, while looking through the eyepiece.

Further, Japanese Laid-open Patent Application No. HEI 3(1991)-218744 proposes the apparatus which is arranged with an image detecting means at a position diverged from the optical system of a binocular stereo microscope to display the anterior eye to be operated on and the reticule or a scale and the like on a monitor, so that the alignment of the stereo microscope will be performed by putting the reticule and the like over the anterior eye on the monitor.

However, in the former method inserting a reticule into one eye of the eyepiece part of the binocular stereo microscope, both the right and left optical axis of the observation optical system in the binocular stereo microscope are inclined at an angle respectively to a line linking an apex and a curvature center of a cornea. Therefore, it is difficult to put a reticule over an image of the anterior eye precisely under the influence of the diopter of the stereo microscope and achieve focusing accuracy according to an inclination of respective optical axis of the observation optical system.

In the latter alignment method using a monitor, because of arranging an image detecting means coaxially with the optical axis linking the apex and the curvature center of cornea of the patient's eye, it is possible to prevent the positional deviation between the reticule and the image of anterior eye caused by the inclination of the optical axis. But whether the anterior eye and the reticule are placed at a proper position on a monitor depend on the observer's judgement, and the alignment condition depend on the intuition and the experience of the operator handling the binocular stereo microscope. Consequently, a good alignment can be not always obtained. Further, the operator must look at a monitor for alignment and then through an eyepiece for observing the patient's eye in turn.

SUMMARY OF THE INVENTION

The present invention has been made in view of the above circumstances and has an object to overcome the above problems and to provide a binocular stereo microscope with which an alignment may be performed easily and precisely while observing the patient's eye, with the consequence that the operation on the cornea and the like can be achieved safely.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, a as embodied and broadly described herein, a binocular stereo microscope including an observation optical system to observe the patient's eye through binocular vision of the present invention comprises a laser transmitting optical system for transmitting the therapeutic laser beam coaxially with the optical axis of an objective lens in the binocular stereo microscope to the patient's eye, an alignment light beam projection optical system for projecting the alignment light beam onto the patient's eye to form an alignment index on the eye, detecting means for detecting the index image projected on the patient's eye by the alignment light beam projection optical system, judging means for judging an alignment situation based on the image detected by the detecting means, and moving means for moving the patient's eye relatively to the binocular stereo microscope based on a result judged by the judging means.

In another aspect of the present invention, a cornea operation apparatus using a binocular stereo microscope comprises an alignment light source for emitting alignment light beam, an alignment light beam projection optical system for projecting the alignment light beam emitted from the alignment light source on a cornea of the patient's eye, a laser source for emitting a therapeutic laser beam, a therapeutic optical system for projecting the therapeutic laser beam emitted from the laser source onto the cornea of the patient's eye, a microscopic observation optical system for transmitting the observation light beam projected on the cornea toward the operator's eye through a microscope, cornea reflecting image position detecting means, which branches from the alignment light projection optical system, for detecting a position of a cornea reflecting image through the reflected light of alignment light projected on the cornea of the patient's eye, alignment information judging means for judging alignment information of the patient's eye based on a signal detected by the cornea reflecting image position detecting means, alignment information displaying means for displaying optically the alignment information judged by the alignment information judging member, alignment information transmitting means for transmitting the alignment information displayed by the alignment information displaying means to the operator's eyes, the alignment information transmitting means branching from the microscopic observation optical system.

According to the present invention, it is possible to perform the alignment easily and precisely while looking through a microscope in accordance with the alignment information displayed by a displaying device provided in the microscope without translating the operator's visual line in turn.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
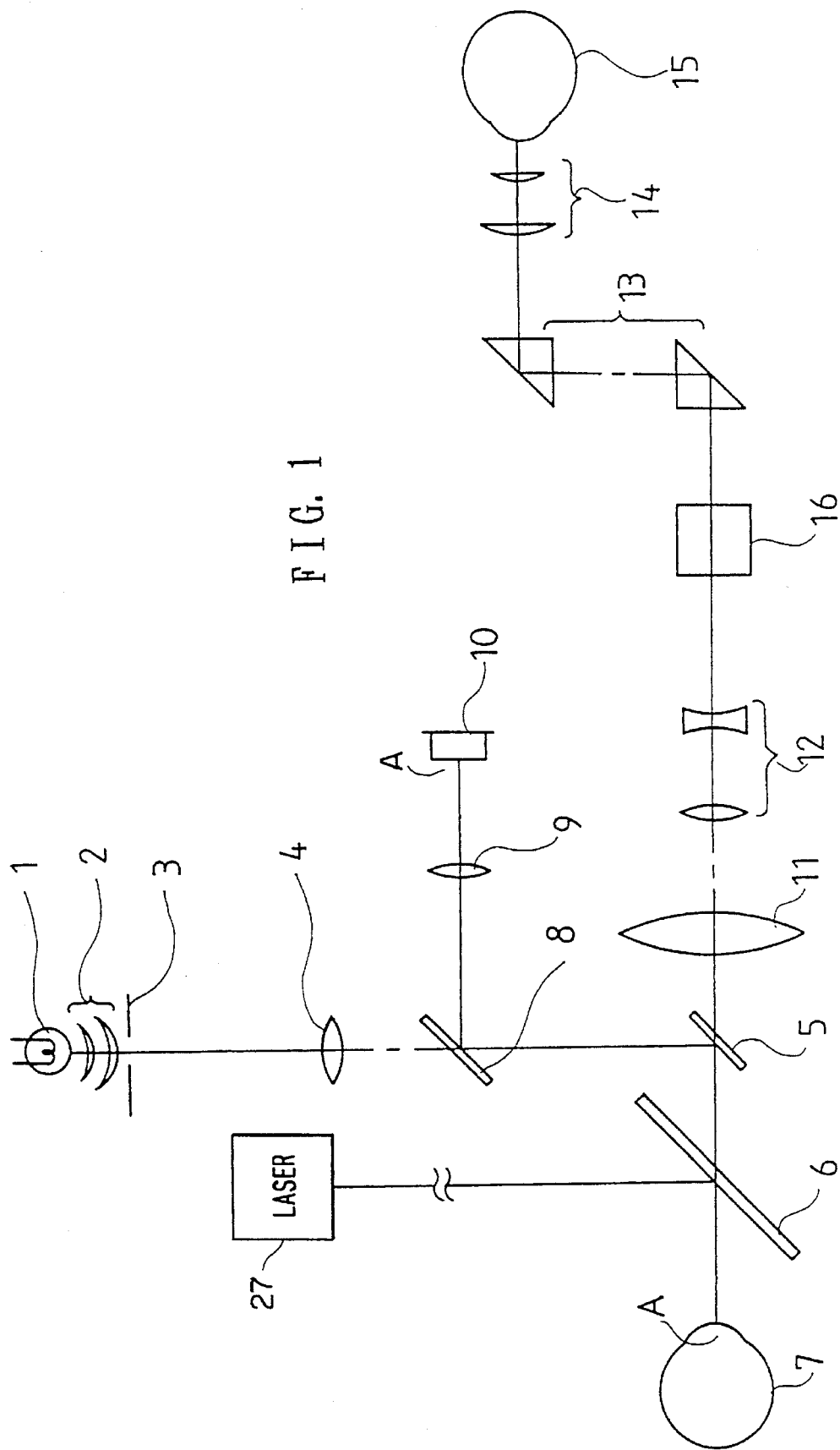
FIG. 1 is a diagrammatic side view of the optical arrangement in the embodiment embodying the present invention.
Figure 2:
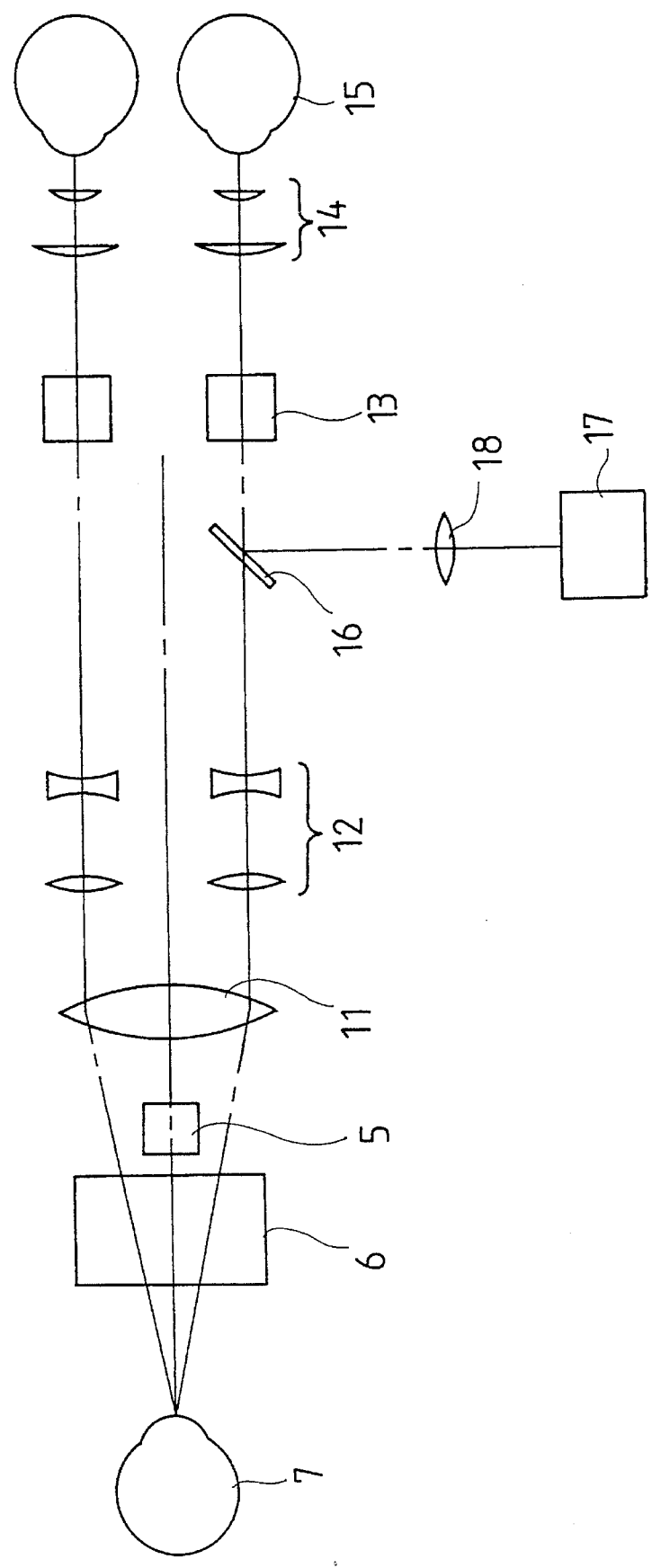
FIG. 2 is a diagrammatic plan view of the optical arrangement of FIG. 1.

A detailed description of one preferred embodiment of a binocular stereo microscope embodying the present invention will now be given referring to the accompanying drawings. FIG. 1 shows a schematical diagram from the side of an arrangement of the optical system in this embodiment, and FIG. 2 shows a plane diagram of FIG. 1.

In FIG. 1, the alignment light projection optical system for projecting an alignment light beam toward the patient's eye to project an alignment index on the patient's eye is provided with a light source 1 for emitting an alignment light to form an image to be reflected by a cornea, a condenser lens 2, a diaphragm 3 with a spot aperture in a center thereof, a collimating lens 4, a reflecting mirror 5, and a dichroic mirror 6.

The alignment light emitted from the light source 1 is condensed through the condenser lens 2 to irradiate the diaphragm 3, transmitted through the aperture of the diaphragm 3, and converted to a parallel luminous flux by the collimating lens 4. The luminous flux reflected by the reflecting mirror 5 is projected onto a cornea of the patient's eye 7 through the dichroic mirror 6. The optical axis of alignment light reflected by the mirror 5 of the alignment optical system becomes coaxial with the optical axis of an objective lens of an observation optical system mentioned later. Additionally, the dichroic mirror 6 is covered with a film capable of reflecting a laser beam, but transmitting visible light on its surface. The therapeutic light such as an excimer laser emitted from an excimer laser source 27 of FIG. 1 and the like is reflected by the dichroic mirror 6 toward the patient's eye 7.

The luminous flux of alignment light projected on a cornea of the patient's eye 7 forms a virtual image A of the specular reflection of the cornea. In a precise alignment, the virtual image is formed at a position of half of the radius of curvature from the apex of the cornea on a line from an apex through a center of curvature of the cornea.

It is not necessary that a luminous flux to be projected on the cornea is always parallel luminous flux, if the transmitting optical system of the therapeutic light is only designed in consideration of that the luminous flux is translated on the optical axis of the patient's eye according to an expansion angle of the luminous flux.

The alignment light reflected by the patient's eye is transmitted through a dichroic mirror 6, and reflected by a mirror 5 toward a beam splitter 8 disposed on the optical axis of the alignment optical system. The luminous flux of the alignment light from virtual image A is reflected by the beam splitter 8 and is focused on a two-dimensional CCD 10 through a focusing lens 9, so that a position of the virtual image A as a cornea reflecting image may be detected through the two-dimensional CCD 10.

The alignment light reflected by the cornea is also transmitted to the observation optical system through a dichroic mirror 6 so as to be observed by the operator.

In the observation optical system of the binocular stereo microscope, there is an objective lens 11, a pair of variable power optical systems 12, a pair prisms 13, a pair of eyepieces 14 for the operator's right and left eyes 15 respectively, and a beam splitter 16 on the one optical axis (of left eye side in this embodiment) of the observation optical system as shown in FIG. 2.

Figure 3:
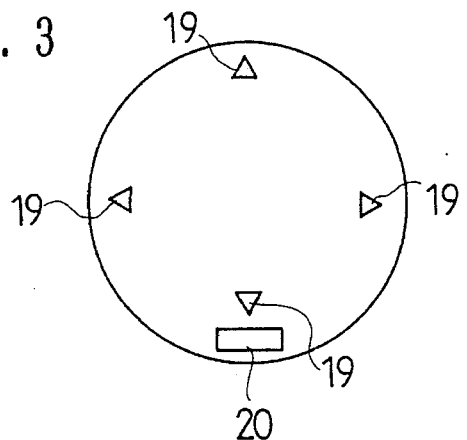
FIG. 3 is a schematic view of showing the visual field of a binocular stereo microscope according to the present invention.

As shown in FIG. 2, the beam splitter 16 disposed on the optical axis of the observation optical system makes an optical axis of luminous flux of the indexes 19 and 20 and the like (referring to FIG. 3) emitted from a displaying device 17 coaxial with the optical axis of the observation optical system by reflecting the luminous flux toward the operator's eye 15.

The displaying device 17 displays alignment position information detected by the two-dimensional CCD 10 with indexes 19 and 20. That is, one of the triangle indexes 19 indicates the deviating direction of alignment by turning on a light emitting diode (not shown) and an index 20 indicates a deviation in the optical axis direction, The luminous flux of these triangle indexes 19 and index 20 forming the displaying device 17 are projected onto the beam splitter 16 through a projective lens 18, and reflected by the beam splitter 16 toward the operator's eye 15, so that the observer can look at the alignment position information on a display screen of the displaying device 17 through an eyepiece 14.

Figure 4:
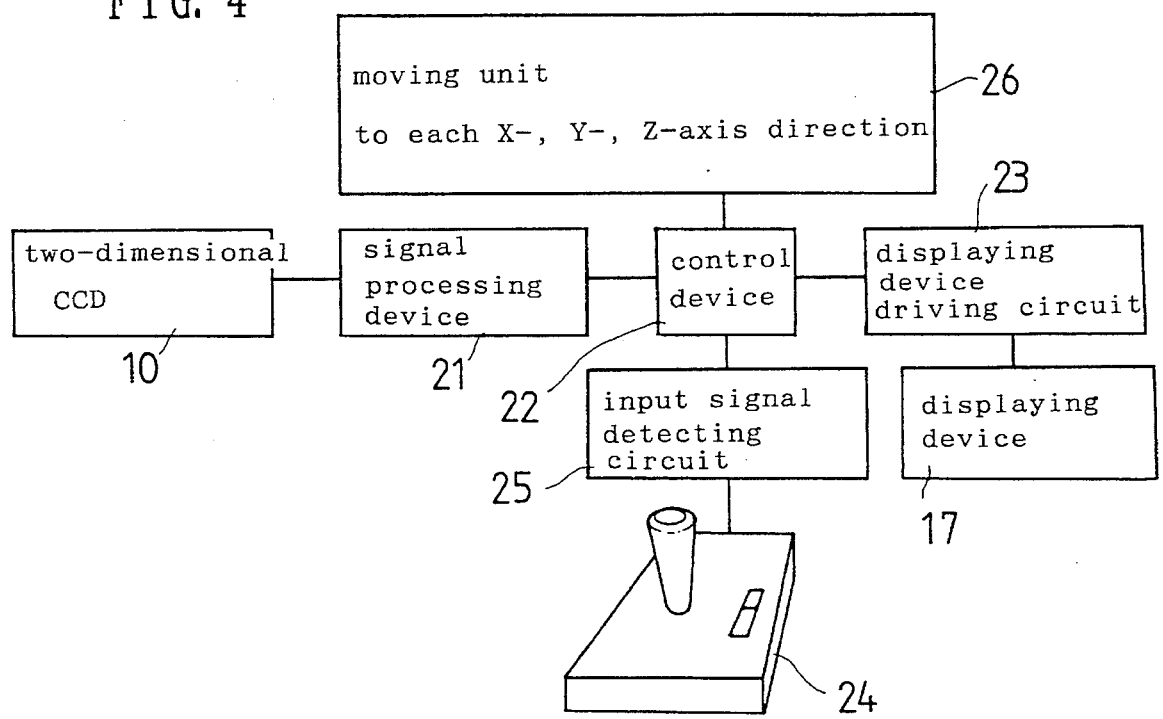
FIG. 4 is an electrical block schematic diagram of explaining an alignment information displaying function of the present embodiment.

FIG. 4 shows an electrical block diagram to display the alignment information in the displaying device 17. An information signal from two-dimensional CCD 10 is input into a signal processing device 21, and a signal about a center position and area of an image A found through an operation of the signal processing device 21 is introduced to a control device 22 comprising a microcomputer and the like.

In the control device 22, the deviation degree on all sides, i.e. upper or lower, right or left sides direction and on vertical direction along the optical axis with respect to the patient's eye, are found by comparing the output signal from the signal processing device 21 with information stored in the control device 22 in advance.

The signal of deviation degree on plane and on the optical axis direction found in the control device 22 is introduced into a displaying device driving circuit 23 to operate the displaying device 17 displaying such deviation degree on the display screen with the indexes 19 or 20.

In accordance with the signal displayed by the displaying device 17, the binocular stereo microscope will be moved relatively with the patient's eye so as to be placed in a proper position with the patient's eye, but generally a supporting member for supporting the patient's eye in the operation apparatus will be moved. Plus or minus of the deviation degree in the optical axis direction may be judged by comparing the increase or decrease of deviation degree with respect to the moving direction.

To move the binocular stereo microscope and the patient's eye relatively, an input unit 24 provided with a joystick and a couple of push switches is operated by the operator in accordance with the index displayed by the displaying device 17.

An input signal detecting circuit 25 detects the inclining direction and degree of the joystick operated by the operator to introduce into the control device 22 as the movement data toward an upper or lower, right or left direction, similarly the pushed switch and its pushing time by the operator to introduce into the control device 22 as the movement data toward a vertical direction.

Based on the moving data detected by the input signal detecting circuit 25 as described above, the moving unit 26 for moving the patient's eye in each X-, Y-, Z-axis direction is driven through a control device 22 to move a binocular stereo microscope or a supporting member to a proper direction.

Figure 5:
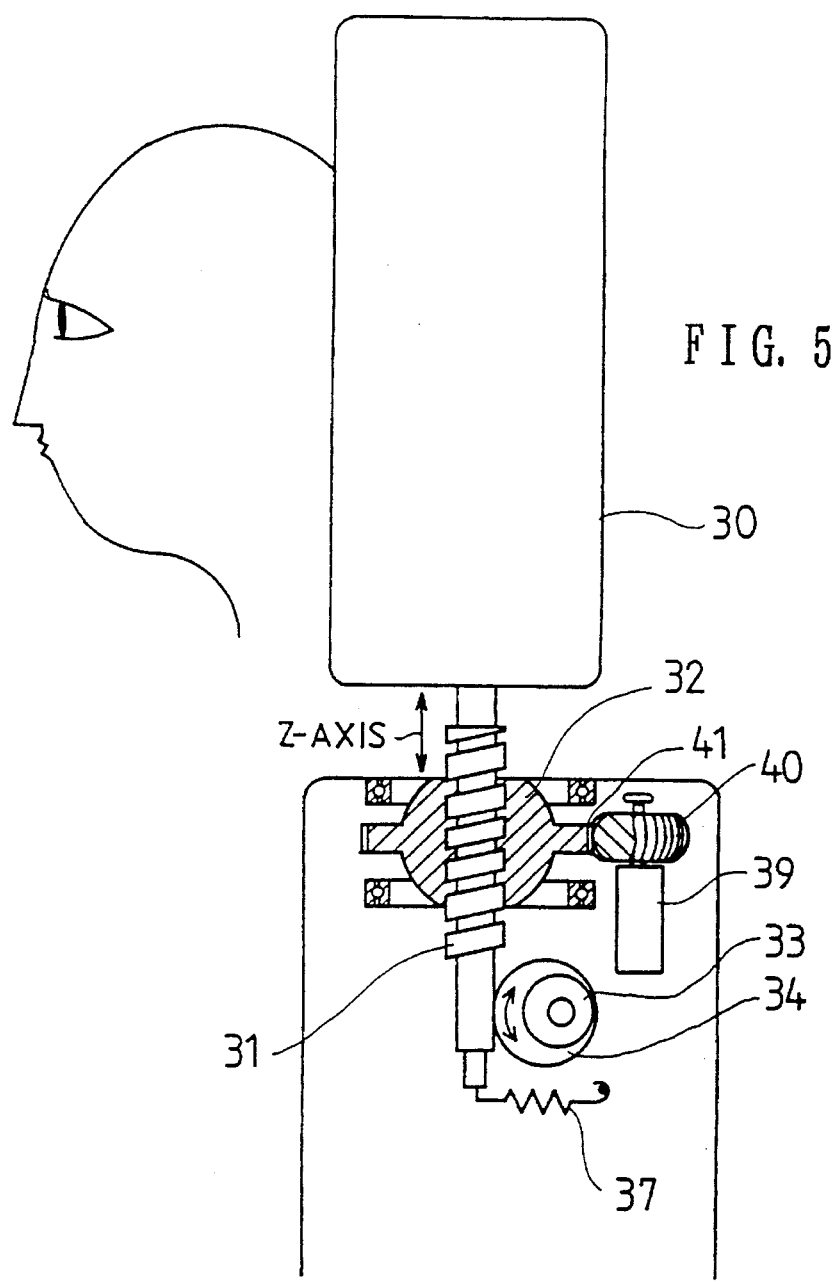
FIG. 5 is a schematic view showing an example of movement structure of a supporting member in an embodiment.
Figure 6:
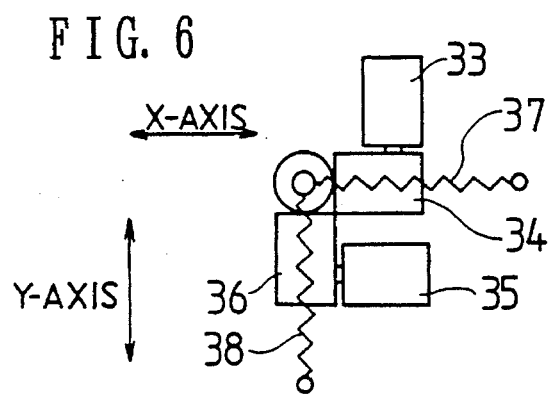
FIG. 6 is a fragmentary schematic view of showing the movement structure of FIG. 5 in another direction.

FIG. 5 and FIG. 6 show a specimen of the movement structure to move the supporting member for the patient's eyes. The supporting member 30 is connected to an end of a feed screw 31 supported through a spherical bearing 32. The feed screw 31 is, additionally, supported by a cam 34 of a motor 33 for moving the supporting member 30 in the X-axis direction and a cam 36 of a motor 35 for moving the same in the Y-axis direction respectively against each stretch power of springs 37 and 38. A main driving gear 40 of a motor 39 for moving the supporting table 30 in the Z-axis direction is interlocked with the feed screw 31 through an inverted driving gear 41 of the spherical bearing 32.

Accordingly, the supporting member 30 can be moved to X-axis direction by driving the motor 33 to rotate the cam 34, or to Y-axis direction by driving the motor 35 to rotate the cam 36, and also to Z-axis direction by driving a motor 39 to rotate the main driving gear 41 through the spherical bearing 32.

While a two-dimensional CCD is used as a position detecting element in the present embodiment, it is possible to detect the position with a couple of one-dimensional CCD'S instead of a two-dimensional CCD by separating the luminous flux through a beam splitter, and to detect the deviation in a plane with respect to the patient's eye using a photodiode, for example, a quarter division element or position detecting element (PSA).

In the above embodiment, the deviation a plane is indicated by lighting on triangle index 19 so as to be recognized at a glance, for which a letter index can substitute. Additionally, not only one image but also plural images may be used as the cornea reflecting image.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An alignment device for aligning an ultra-violet laser with a patient's eye having a cornea so that the laser can ablate the cornea, the alignment device comprising:

a light source emitting light;

means for transmitting the light to the cornea;

means for monitoring light reflected from the cornea and for providing an indication light beam indicating the three-dimensional position of the cornea, the indication light beam designating a direction in which the cornea should be moved;

an optical system including a stereo binocular microscope for directly and optically observing a front portion of the eye, enabling a direct observation of the patient's eye in the absence of an analysis means; and means for guiding the indication light beam to an operator's eye, including a beam splitter disposed in an observing optical path of said optical system.

2. An alignment device according to claim 1 further comprising means for moving the eye in each of an X-axis, Y-axis, and Z-axis direction in relation to the laser.

3. An alignment device according to claim 1 further comprising means for moving the laser in each of an X-axis, Y-axis, and Z-axis direction in relation to the eye.

4. The alignment device according to claim 1 wherein the stereo binocular microscope comprises an objective lens having a same optical axis as that of the means for transmitting the light to the cornea.

5. The alignment device according to claim 4 wherein the means for transmitting the light to the cornea comprises a dichroic mirror.

6. The alignment device according to claim 1 wherein the means for monitoring the light reflected from the cornea comprises a two-dimensional charge coupled device.

7. An alignment device for aligning an ultra-violet laser with a patient's eye having a cornea so that the laser can ablate the cornea, the alignment device comprising:

a light source emitting light;

means for transmitting the light to the cornea;

means for monitoring light reflected from the cornea and for providing a first signal indicating the three-dimensional position of the cornea, the first signal designating a direction in which the cornea should be moved;

means for comparing the first signal with a stored second signal and for generating a third signal indicating a deviation in the position of the cornea;

means for displaying the third signal;

an optical system including a stereo binocular microscope for directly and optically observing the eye, enabling a direct observation of the patient's eye in the absence of an analysis means; and means for guiding an indication of the three-dimensional position of the cornea to an operator's eye, including a beam splitter disposed in an observing optical path of said optical system.

8. An alignment device according to claim 7 further comprising means for moving the eye in each of an X-axis, Y-axis, and Z-axis direction in relation to the laser.

9. An alignment device according to claim 7 further comprising means for moving the laser in each of an X-axis, Y-axis, and Z-axis direction in relation to the eye.

10. The alignment device according to claim 7 wherein the stereo binocular microscope comprises an objective lens having a same optical axis as that of the means for transmitting the light to the cornea.

11. The alignment device according to claim 10 wherein the means for transmitting the light to the cornea comprises a dichroic mirror.

12. The alignment device according to claim 10 wherein the means for comparing comprises a processor.

13. A method of aligning an ultra-violet laser with a patient's eye having a cornea so that the laser can ablate the cornea, the method comprising the steps of:

emitting a light;

transmitting the light to the cornea so that the light reflects from the cornea;

monitoring the light reflected from the cornea;

providing an indication of the three-dimensional position of the cornea, the indication designating a direction in which the cornea should be moved;

directly and optically observing the cornea with an optical stereo microscope, enabling a direct observation of the patient's eye in the absence of an analysis means and simultaneously observing the indication of the three-dimensional position of the cornea; and changing the relative position of the laser and the cornea.

14. The method according to claim 13 wherein the step of indicating the position of the cornea comprises the sub-steps of:

generating a first signal in response to the monitoring of the position of the cornea;

comparing the first signal with a stored second signal;

generating a third signal indicating the deviation of the position of the cornea in response to the comparison of the first and second signals; and displaying the third signal.

15. An alignment device for aligning an excimer laser with a patient's eye having a cornea so that the excimer laser can operate on the cornea, the alignment device comprising:

an optical system including a stereo binocular microscope for directly and optically observing a front portion of the eye with an optical stereo microscope, enabling a direct observation of the patient's eye in the absence of an analysis means;

a light source emitting light;

means for transmitting the light to the cornea, including a reflecting mirror, disposed in the optical system, but not in an observing optical path;

monitoring means for monitoring light reflected from the cornea via the reflecting mirror;

display means for displaying an indication of the three dimensional position of the cornea from a signal of the monitoring means, the indication designating a direction in which the cornea should be moved; and means for guiding a beam of the display means to an operator's eye, including a beam splitter disposed in the observing optical path.

* * * * *

UNITED STATES PATENT AND TRADEMARK OFFICE
CERTIFICATE OF CORRECTION

PATENT NO. : 5,571,108
DATED : November 5, 1996
INVENTOR(S) : Masanori AMANO et al.

It is certified that error appears in the above-indentified patent and that said Letters Patent is hereby corrected as shown below:

Claim 5, col. 6, line 27 after "mirror" insert --reflecting radiation emitted by the laser and transmitting the light--.

Claim 11, col. 6, line 65 after "mirror" insert --reflecting radiation emitted by the laser and transmitting the light--.

Signed and Sealed this

Sixth Day of May, 1997

*Attest:*

BRUCE LEHMAN

*Attesting Officer*  Commissioner of Patents and Trademarks